United States Patent [19]
Stratton

[11] Patent Number: 5,437,286
[45] Date of Patent: Aug. 1, 1995

[54] INSTANT-ON, U-SHAPED CONDOM HOLDER PACKAGE

[76] Inventor: Alexander K. Stratton, 3912 N. Cactus Blvd., Tucson, Ariz. 85716

[21] Appl. No.: 192,348

[22] Filed: Feb. 7, 1994

[51] Int. Cl.⁶ .............................................. A61F 6/04
[52] U.S. Cl. .................... 128/844; 128/842; 128/918; 604/347; 604/351; 206/69
[58] Field of Search ............... 128/844, 842, 830, 918; 206/69, 364; 604/352, 351, 349, 347

[56] References Cited

U.S. PATENT DOCUMENTS

| | | | |
|---|---|---|---|
| 2,365,556 | 12/1944 | Karg | 206/63.2 |
| 3,282,414 | 11/1966 | Penksa | 206/63.2 |
| 3,677,225 | 7/1972 | Czirely | 128/132 |
| 4,305,161 | 12/1981 | Diaz | 604/347 |
| 4,738,357 | 4/1988 | Martin et al. | 206/69 |
| 4,875,491 | 10/1989 | Parrone | 128/844 |
| 4,961,734 | 10/1990 | Kassman | 604/349 |
| 5,002,057 | 3/1991 | Brady | 206/69 |
| 5,044,492 | 9/1991 | Auerbach | 206/66 |
| 5,117,841 | 6/1992 | McBeth | 128/844 |
| 5,316,019 | 5/1994 | Jones | 128/844 |

FOREIGN PATENT DOCUMENTS

| | | | |
|---|---|---|---|
| 2249295 | 6/1992 | United Kingdom | 128/844 |
| 8802624 | 4/1988 | WIPO | 604/349 |
| 9206657 | 4/1992 | WIPO | 128/844 |
| 9220595 | 11/1992 | WIPO | 206/69 |
| 9321873 | 11/1993 | WIPO | 128/844 |

*Primary Examiner*—Robert A. Hafer
*Assistant Examiner*—Michael O'Neill
*Attorney, Agent, or Firm*—Victor Flores

[57] ABSTRACT

A condom holder package including a condom member, a condom carriage member having a U-shaped condom holder portion, and rupturable inner and outer packaging film members. Outer packaging surface treatment is provided to identify and to assure proper wear orientation of the packaged condom. The condom member is neatly gathered in a ready-to-use state about the U-shaped condom holder. The U-shaped configuration of the condom holder departs from traditional annular condom holders, and facilitates an unimpeded lateral removal of the condom holder from a positioned condom. The laterally removable U-shaped condom holder configuration, carrying a ready-to-use condom, along with the rupturable packaging film members produce an instant-on condom product.

4 Claims, 3 Drawing Sheets

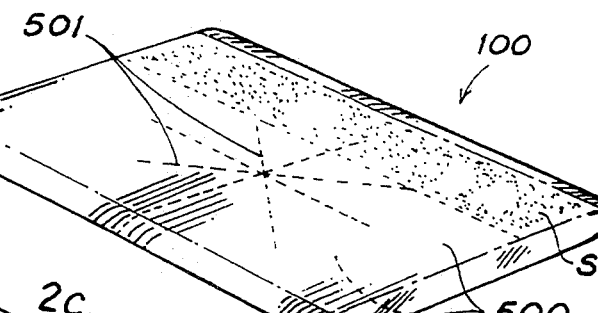
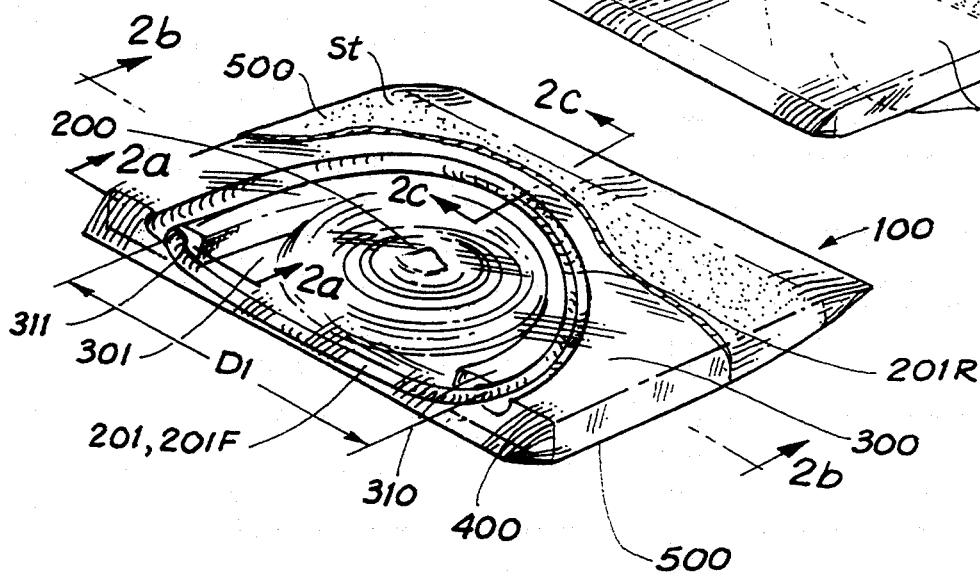
FIG. 1b
FIG. 1a
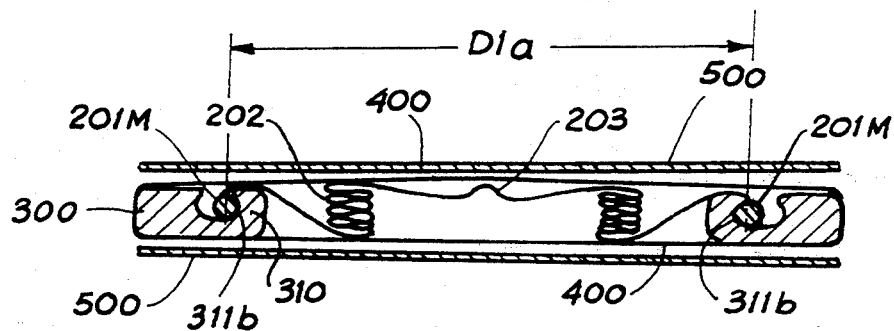
FIG. 2b
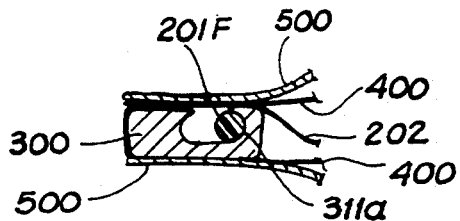
FIG. 2a
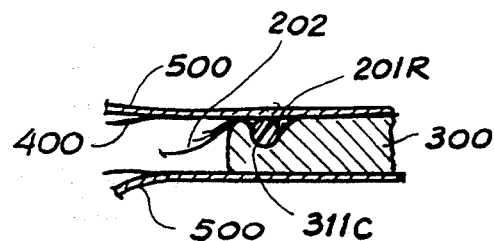
FIG. 2c

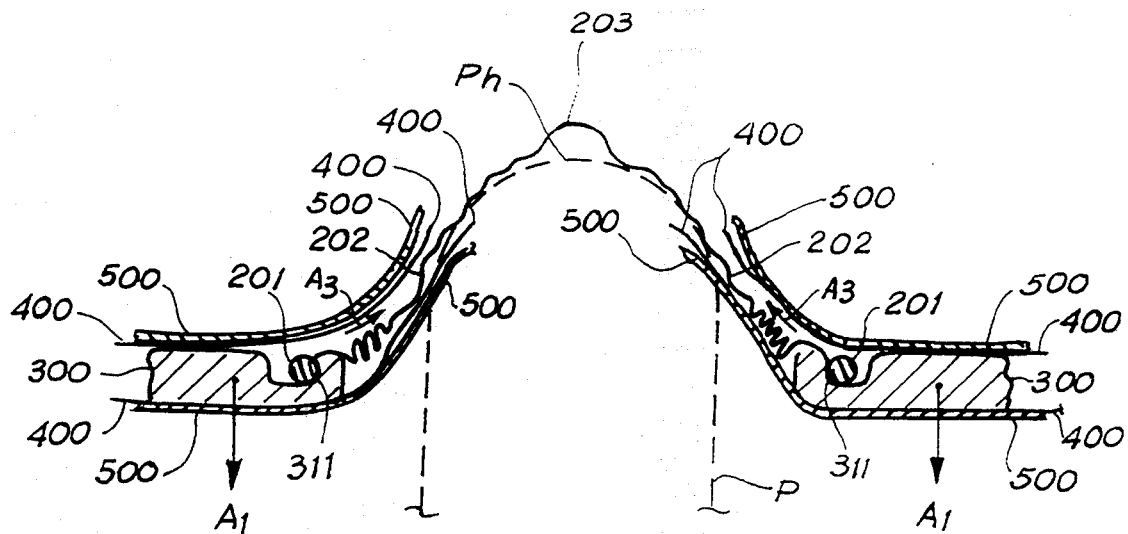
FIG. 3a
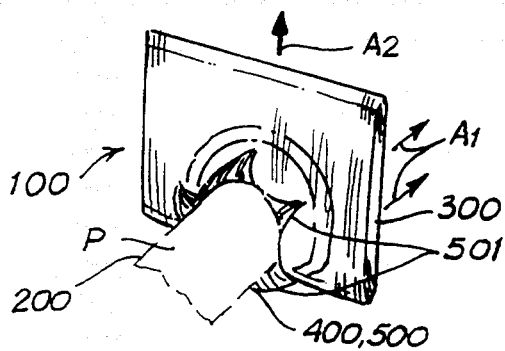
FIG. 3b
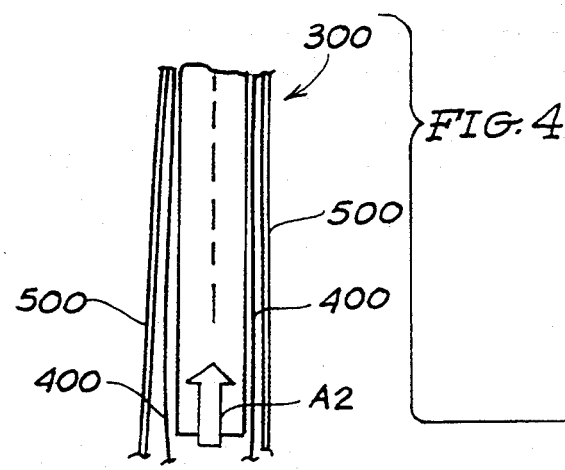
FIG. 4
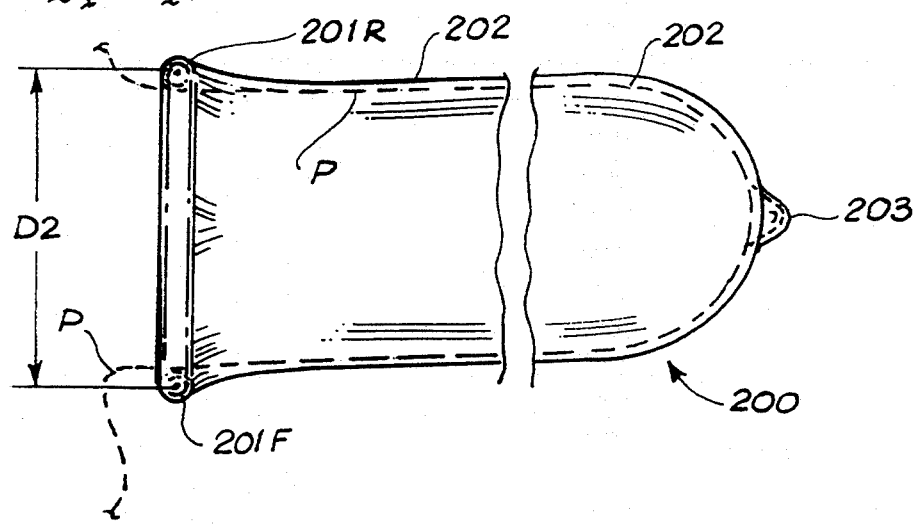

INSTANT-ON, U-SHAPED CONDOM HOLDER PACKAGE

FIELD OF THE INVENTION

This invention relates to condoms. More particularly, the present invention relates to condoms and their packaging structure. Even more particularly, the present invention relates to condoms and their holding and packaging structural features which address negative aspects of using a condom, i.e. structural features that address condom's packaging configurations that prolongs the time for positioning the condom on a user and that detract from condoms being more widely used, including structural features that relate to removal of the condom holders after being positioned on a user.

BACKGROUND OF THE INVENTION

The following group of patents are representative of patents that have dealt with the problem to which the present invention pertains.

| U.S. Pat. No. | Inventor | Date of Issue |
|---|---|---|
| 2,365,556 | F. G. Karg | March 12, 1941 |
| 3,282,414 | S. Penksa | March 12, 1965 |
| 3,677,225 | J. Czirely | July 18, 1972 |
| 4,738,357 | Martin et al. | April 19, 1988 |
| 4,875,491 | Parrone | October 24, 1989 |
| 4,961,734 | Kassman | October 9, 1990 |
| 5,044,492 | Auerbach | September 3, 1991 |
| 5,117,841 | C. R. McBeth | June 2, 1992 |

Of the patents listed above, the closest patents relating to the present invention are U.S. Pat. Nos. 4,738,357, 4,875,491 and 5,044,98. U.S. Pat. No. 4,875,491 states the same objective as the present invention, i.e. to provide a condom that does not counter the prevailing mood prior to its use and teaches several annular embodiments for mounting a condom, including means for making the condom more easily positioned, and condom holding means that are removable by reversing over the male organ, or by lateral removal after spreading the split-ring annular holder. U.S. Pat. No. 4,738,357 teaches an annular condom holder device wherein a condom is rolled, or folded, within a C-shaped annular holder. The condom and ring being covered by two protective disks at opposing sides. One of the disks being outwardly pressable, while the other disk being destructible during initial application. The condom holder of the '357 patent must be removed by reverse action over the user's penis, or left in place during intercourse. U.S. Pat. No. 5,044,498, as well as U.S. Pat. No. 4,738,357, teach adapting the exterior portion of the condom container with marks or projections for distinguishing the sides of the package by the sense of touch to assure proper orientation of the enclosed condom.

While the prior art has provided condom holders in structure that reduce the condom application time, the prior art has not provided a condom holder that, not only reduces the condom application time, but that also eliminates efforts associated with removal of the condom holder after the condom has been positioned. The prior art's teachings of annular condom holders are deemed as teachings of inadequate structures for effortless removal of the condom holder. Although lateral removal is taught by the '491 patent on a split-ring condom holder, the spreading ring action is viewed as requiring concentrated effort to effect removal of the condom holder.

An article entitled "CDC Advocates Use of Condoms In Blunt AIDS-Prevention Spots", Wall Street Journal, B1, Jan. 5, 1994, exemplifies that a need still exists for making a condom more easily worn. The Wall Street articles make reference to an ad which states "It would be nice if latex condoms were automatic. But since they are not, using them should be.".

Thus, a need is seen to exist for a condom holder apparatus that not only reduces the condom application time, but that also eliminates efforts associated with removal of the condom holder after the condom has been positioned.

SUMMARY OF THE INVENTION

Accordingly, the primary object of the present invention is to provide a condom holder apparatus that not only reduces the condom application time, but that also eliminates efforts associated with removal of the condom holder after the condom has been mounted.

A related object of the present invention is to provide a condom holder apparatus, as in the primary object, with the object of promoting use of condoms to prevent the spread of AIDS.

The foregoing objects are accomplished by providing a condom package comprising three basic parts, namely a condom member, a condom carriage member having a U-shaped condom holder, or U-shaped condom retainer structure, and inner and outer packaging film member. One of the outer packaging surfaces, or one of the sides of the carriage member, being provided with a surface treatment to identify and to assure proper orientation of the packaged condom. The condom member being a condom that is neatly collapsed and gathered about the U-shaped condom holder. The base ring of the condom, i.e. the open-end, flexible ring portion of the condom, being detachably retained by the U-shaped retainer such that the open-end of the condom is enlarged to facilitate an instant-on configuration. A variably undercut groove on the U-shaped condom holder facilitates an easy disengagement of the condom's flexible ring portion from the holder. The condom member is sanitarily packaged within a laminated-windowed structure. Each laminate comprises an inner and outer film member that mounts to the flat surfaces of the carriage member. The inner and outer film members are provided with appropriate serrations, as required, for effecting an easily rupturable structure. By example, a rupture may be initiated by forcing the condom holder apparatus onto a penis. In this manner of rupturing the film members, the condom's final positioning on the penis is by continuous action facilitated by the structure of the condom holder that properly dispenses the condom. The condom holder portion of the condom carriage is formed having a non-annular, substantially U-shaped opening, designed to facilitate unimpeded lateral removal of the condom holder from the positioned condom. The U-shaped condom holder configuration, along with the foregoing instant-on packaging attributes, accomplish the objects of the invention.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS

FIG. 1a is a cutaway perspective view of the present invention illustrating a condom in an easily removable packaging structure having a U-shaped opening in accordance with the present invention.

FIG. 1b is a perspective view of a packaged condom illustrating the outer packaging serrations and surface treatment features which, in combination, facilitate a user's expediency associated with a sexual encounter and proper wearing orientation of the packaged condom.

FIG. 2a is a partial frontal cross section view taken along line 2a—2a illustrating detachable securement of a condom's open-end flexible ring portion in an undercut groove of the retainer structure that delineates the U-shaped opening on the condom holder.

FIG. 2b is a cross sectional view taken along line 2b—2b in FIG. 1a illustrating a condom packaged in a ready-to-wear state facilitated by detachable securement of a condom's open-end flexible ring portion in an undercut groove of the retainer structure and a folded securement of condom material within an enclosure region formed about the U-shape opening.

FIG. 2c is a cross sectional view taken along line 2c—2c in FIG. 1a illustrating a far end portion of condom's open-end flexible ring portion detachably secured in the shallowest part of an undercut groove of the retainer structure.

FIG. 3a is a user application illustration showing the condom of the present invention being directionally placed onto a user's penis after having easily ruptured the body side outer/inner packaging film members, contacting the condom's closed-end portion, rupturing the non-body side inner/outer film members for continued dispensing of the folded condom material.

FIG. 3b is a user application illustration showing the condom of the present invention fully placed onto a user's penis and also showing the condom carriage member in a state for being removed from the condom member, which removal is facilitated by the U-shaped opening and detachment of the open-end flexible ring portion from the variably undercut retainer structure.

FIG. 4 is a user application illustration showing the condom of the present invention fully placed onto a user's penis and the condom carriage member removed from condom member.

DESCRIPTION OF THE PREFERRED EMBODIMENT

Figure 5:
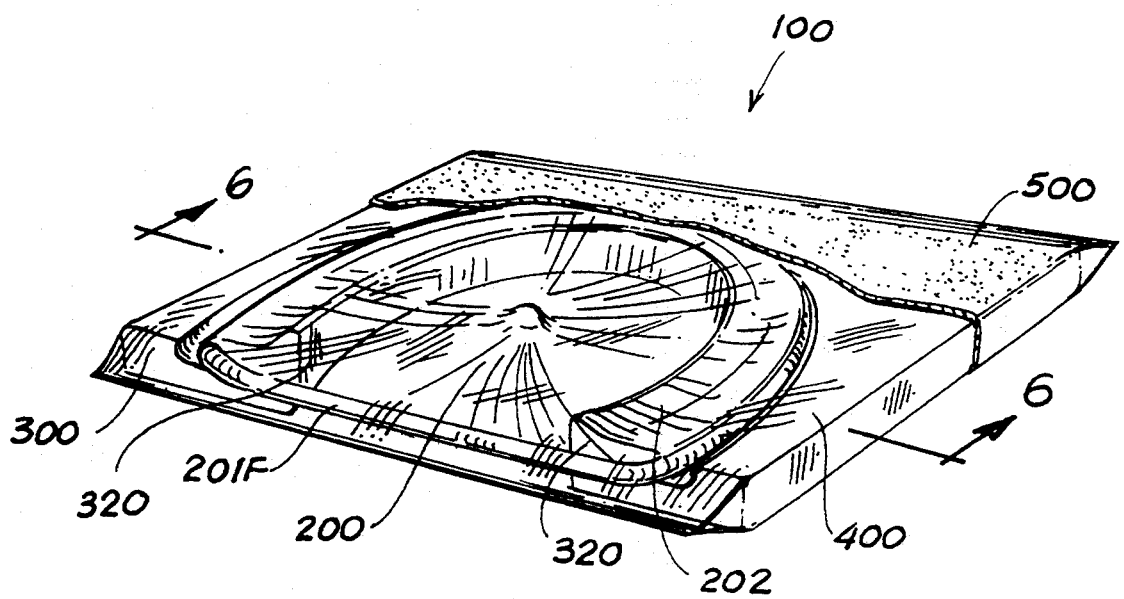
FIG. 5 is a cutaway perspective view of an alternative embodiment of the present invention illustrating a U-shaped condom retainer structure having a variably undercut groove for detachably retaining the open-end flexible ring portion of a condom and a retainer shelf portion for out-of-the-way placement of the folded condom material to assure a user of initial contact of the condom's closed-end portion after rupturing the body side outer/inner packaging film members.

Referring now to the drawings where in FIG. 1a a packaged condom apparatus 100 is shown in a cutaway perspective view. Condom apparatus 100 is shown comprising a condom member 200, a condom carriage member 300 and opposing laminated sets of packaging film member 400 and 500. FIG. 1b shows condom apparatus 100 in a perspective view further illustrating the outer packaging serrations 501 and surface treatment features St which, in combination, facilitate an aspect of the instant-on objective of the present invention. Referring back to FIG. 1a condom apparatus 100 is shown comprising condom carriage member 300 formed in a thin, substantially flat, credit-card-like profile. Carriage member 300 comprises a U-shaped condom holder structure 310 that delineates U-shaped opening 301 which facilitates easy lateral removal of the carriage 300 and packaging films 400, 500 from a fully fitted condom 200, see generally FIG. 3b. Consistent with the objects of the invention, i.e. the instant-on aspect of wearing the condom and the removal of the condom holder from the condom member, the U-shaped retainer structure 310 is designed for detachably retaining the condom's open-end flexible ring portion 201 in a variably undercut groove 311, and for maintaining condom 200 in an enlarged open-end state, denoted by the distance D1. Undercut groove 311 varies in depth such that, as illustrated in FIG. 2a, the frontmost portion 201F of flexible ring 201 fits into the deepest undercut groove 311a, also as illustrated in FIG. 2b, the flexible ring's mid portion 201M fits into a lesser depth undercut groove 311b, and also as illustrated in FIG. 2c, the flexible ring's rear portion 201R fits into the shallowest undercut groove 311c. FIG. 2b also shows the manner in which condom 200 is packaged to yield the ready-to-wear configuration. As illustrated, condom apparatus 100 is in an unused state with opposing inner and outer packaging film members 400, 500 in an unruptured state. In this state, the open-end flexible ring portion 201,201M is retained in the undercut groove 311,311b and maintained in an enlarged states denoted by distance D1a. Further, the condom portion 202 is gathered and folded within the U-shaped enclosed space 301 created by retainer 310 in a manner that facilitates continuous dispensing of the condom material 202, after a penis contacts the condomes closed-end portion 203. Alternatively, condom portion 202 may be gathered entirely within undercut 311.

Referring now to FIG. 3a showing a user application of the present invention. As illustrated, a male's penis P is shown being fitted in the direction A1 with the packaged condom 200 of the present invention. However, it is within the scope of the invention for condom apparatus 100 to be utilized by a female during sexual intercourse for subsequent rupture by a penis and dispensing of the packaged condom 200 by penetration action opposite arrow A1 into the vagina. In this latter type of application, appropriate surface treatment St would indicate proper dispensing orientation of the packaged condom.

Still referring to FIG. 3a, and during use of condom apparatus 100, the outer packaging material of condom apparatus 100 is easily ruptured by forcing, in the direction A1, the properly oriented side of outer packaging film member 500 onto penis head Ph, continued rupturing of inner film 400, contacting the condom's closed-end portion 203, rupturing the non-body side inner film member 400 and outer film 500, and continued dispensing, as indicated by arrow A3 of the folded condom 202 over the penis P. It should be emphasized that during this application period, the open-end flexible ring portion 201 is secured and retained by the undercut groove 311.

FIG. 3b shows the ruptured, fitted state of condom apparatus 100 with condom 200 fully placed onto a user's penis P as indicated by arrows A1. FIG. 3b further shows condom carriage member 300, with ruptured serrations 501 on outer packaging film 500 as well as the ruptured inner film member 400, collectively, in a state for being removed in the direction A2 from the fitted condom member 200. Of particular utility during lateral removal of carriage member 300 is the U-shaped opening 301 delineated by condom retainer structure 310, and the detachable feature of the open-end flexible ring portion 201 from the variably undercut groove 311. The detachment of the flexible ring portion 201 is initiated by a tug as indicated by arrow A2 that first disengages ring portion 201R from the shallow groove 311c and which detachment continues due to the condom's elastic nature. It should be noted that shallow groove 311c facilitates lateral removal of the holder 310 from the condom member 200, as desired by the user, at any time after rupturing the films 400, 500. FIG. 4, in particular, shows the condom carriage member 300 removed from condom member 200. FIG. 4 also shows the fitted condom 200 on a user's penis P, with the open-end flexible ring portion 201F, 201F in a relaxed fitted state having a opening designated by the distance D2 which is less than D1 in the unused state, as shown in FIG. 1a.

Figure 6:
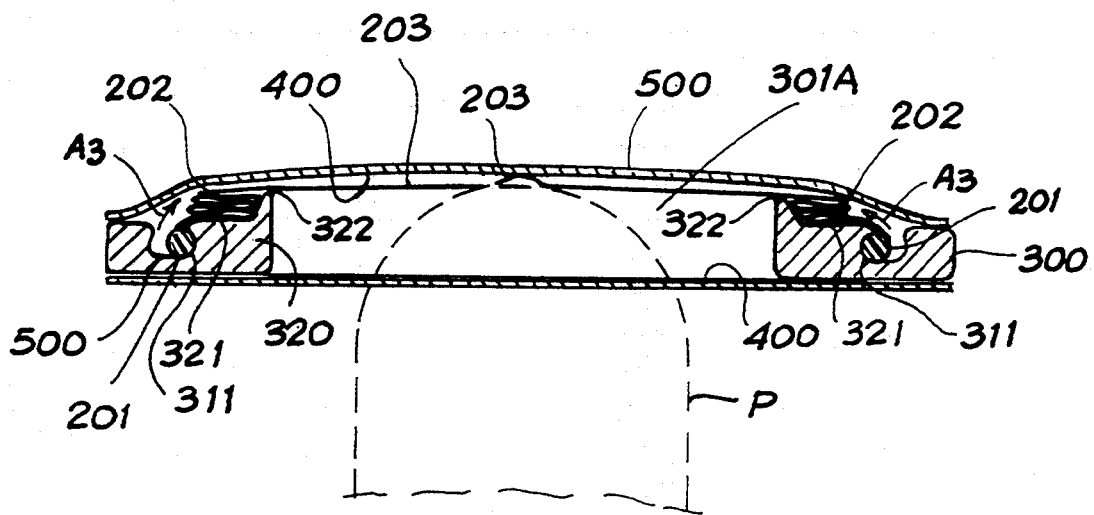
FIG. 6 is a cross sectional view taken along line 6—6 in FIG. 5 illustrating a condom packaged in a ready-to-wear state with the folded condom material packaged on a retainer shelf structure for out-of-the-way dispensing of the condom and to assure that a user will initially contact the condom's closed-end portion after rupturing the body side outer/inner packaging film members, and also showing the condom's open-end flexible ring portion detachably retained in an undercut groove of the retainer structure.

FIG. 5 shows an alternative embodiment 100A of the present invention illustrating a U-shaped condom retainer structure 320 having, not only a variably undercut groove 311 for detachably retaining the open-end flexible ring portion 201 of a condom 200, but also a retainer shelf portion 321 for out-of-the-way placement of the folded condom portion 202 to assure that a user will initially contact the condom's closed-end portion 203 after rupturing the body side outer packaging film members 400, 500. FIG. 6 in particular illustrates, in cross section, condom 200 packaged in a ready-to-wear state with the folded condom material 202 packaged on retainer shelf structure 321 for out-of-the-way, continuous dispensing of the folded condom 202 as indicated by arrow A3. FIG. 6 further shows a penis P amply disposed in the space 301A created by the U-shaped retainer structure 320. As with the condom apparatus 100, the wearing of the condom 200 packaged in condom apparatus 100A is also initiated by first rupturing the body side outer/inner packaging film members 500, 400, followed by continued rupturing of the opposing side's inner/outer packaging film member 400, 500 and continued dispensing of the folded condom material 202 over the rim 322 until the condom 200 is fully fitted. As with embodiment 100, the U-shaped condom retainer structure provided on embodiment 100A facilitates unimpeded lateral removal of the condom holder from the positioned condom.

Therefore, while the present invention has been shown and described herein in what is believed to be the most practical and preferred embodiments, it is recognized that departures can be made therefore within the scope of the invention, which is therefore not to be limited to the details disclosed herein but is to be accorded the full scope of the claims so as to embrace any and all equivalent apparatus.

I claim:

1. A condom carrying apparatus, said apparatus comprising, in combination:
   (A) a condom member, said condom member comprising:
      (a) an open end defined by a flexible ring portion,
      (b) a folded condom material portion, and
      (c) a closed end portion;
   (B) a condom carriage member, said condom member being detachably contained by said condom carriage member, said condom carriage member comprising:
      (a) a U-shaped opening delineated by a U-shaped structure designed for carrying said condom member, said U-shaped structure comprising:
         (i) opposing ends that are spaced apart by a distance that facilitates lateral removal of said condom carriage member from said condom member after application of said condom member onto a user's penis,
         (ii) an undercut groove for supporting said flexible ring portion,
         (iii) a retainer shelf portion adjacent said groove for supporting said folded condom material portion, and
         (iv) a wall structure adjacent said shelf portion, said wall structure forming a walled periphery about said U-shaped-opening; and
   (C) at least one set of opposing, rupturable primary packaging film members attached to said carriage member to sanitarily cover said contained condom member,
   said flexible ring portion being releasably retained about said undercut groove, said folded condom material portion being disposed on said retainer shelf portion, and said condom's closed-end portion being disposed beyond said walled periphery about said U-shaped opening,
   said undercut groove having a variable depth undercut that facilitates releasably retaining said flexible ring portion in an enlarged open state during storage and application of said condom member, said variable depth undercut comprising a shallow portion that facilitates release of said condom member from said U-shaped opening structure upon applying a disengagement force to laterally remove said condom member from said carriage member.

2. A condom carrying apparatus as described in claim 1, said apparatus further comprising:
   at least one serrated, rupturable outer packaging film member attached over one of said at least one set of opposing primary packaging film members.

3. A condom carrying apparatus, as described in claim 1, wherein:
   said carriage member comprises a thin, substantially flat, credit-card like structure having a discernable surface treatment on one side to properly orient a user to a correct wearing orientation of said condom member.

4. A condom carrying apparatus as described in claim 3, further comprising:
   at least one serrated, rupturable outer packaging film member attached over one of said opposing primary packaging film members.

* * * * *